US007327823B2

(12) United States Patent
Matsuura

(10) Patent No.: US 7,327,823 B2
(45) Date of Patent: Feb. 5, 2008

(54) RADIATION IMAGE PROCESSING APPARATUS, RADIATION IMAGE PROCESSING METHOD, PROGRAM, AND COMPUTER-READABLE MEDIUM

(75) Inventor: Tomohiko Matsuura, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 353 days.

(21) Appl. No.: 10/969,876

(22) Filed: Oct. 22, 2004

(65) Prior Publication Data

US 2005/0111614 A1    May 26, 2005

(30) Foreign Application Priority Data

Nov. 5, 2003  (JP) .............. 2003-375463

(51) Int. Cl.
*G01N 23/00* (2006.01)
(52) U.S. Cl. .............. 378/8; 378/901; 382/107; 382/131
(58) Field of Classification Search ............ 378/4, 378/8, 95, 162, 901; 382/131, 107, 154
See application file for complete search history.

(56) References Cited

U.S. PATENT DOCUMENTS

| 4,858,128 A | 8/1989 | Nowak ............... 364/413.13 |
| 5,023,894 A * | 6/1991 | Yamashita et al. ............ 378/4 |
| 6,853,701 B2 * | 2/2005 | Cherek et al. ............... 378/16 |
| 7,003,069 B2 * | 2/2006 | Tsujii ............................. 378/8 |
| 7,130,377 B2 * | 10/2006 | Matsuno ..................... 378/96 |
| 2006/0133564 A1 * | 6/2006 | Langan et al. ................ 378/8 |

FOREIGN PATENT DOCUMENTS

| JP | 11-151232 | 6/1999 |
| JP | 2002-365239 | 12/2002 |

OTHER PUBLICATIONS

Kakadiaris, I., et al., "*Inferring 2D Object Structure from the Deformation of Apparent Contours*," Computer Vision and Image Understanding Academic Press, San Diego, CA, USA, vol. 65, No. 2 (1997), pp. 129-147, XP004464103, ISSN 1077-3142.

* cited by examiner

*Primary Examiner*—Jurie Yun
(74) *Attorney, Agent, or Firm*—Fitzpatrick, Cella, Harper & Scinto

(57) ABSTRACT

In a radiation image processing apparatus and method, body movement information of a subject to be inspected is extracted during CT scanning. It is then determined whether or not a repeat radiograph is required based on the body movement information of the subject. If it is determined that a repeat radiograph is not required, a CT image is reconstructed from projection images. If it is determined that a repeat radiograph is required, the need for a repeat radiograph is instructed.

15 Claims, 12 Drawing Sheets

START
↓
S301 SELECT REPRESENTATIVE IMAGES
↓
S302 EXTRACT POSITIONS OF DIAPHRAGM FROM ALL REPRESENTATIVE IMAGES
↓
S303 CALCULATE CHANGE IN POSITION OF DIAPHRAGM BETWEEN ADJACENT IMAGES
↓
END

| IMAGE No. | CHANGE |
|---|---|
| 1 | 0.6 |
| 2 | 0.2 |
| 3 | 0.1 |
| 4 | 0.5 |
| 5 | 0.1 |
| ⋮ | ⋮ |

RADIATION IMAGE PROCESSING APPARATUS, RADIATION IMAGE PROCESSING METHOD, PROGRAM, AND COMPUTER-READABLE MEDIUM

This application claims priority from Japanese Patent Application No. 2003-375463 filed Nov. 5, 2003, which is hereby incorporated by reference herein.

BACKGROUND OF THE INVENTION

1. Field of the Invention

The present invention relates to a radiation image processing apparatus, a radiation image processing method, a program, and a computer-readable medium for producing computed tomography (CT) images by CT reconstruction based on a plurality of projection images taken by using a two-dimensional sensor. In particular, the present invention relates to a radiation image processing apparatus, a radiation image processing method, a program, and a computer-readable medium in which the need to repeat a radiograph is determined by detecting a movement of a subject to be inspected based on the projection images.

2. Description of the Related Art

In CT radiography, it is known that, if a subject to be inspected moves during CT scanning, appropriate CT images for CT reconstruction usually cannot be achieved. To solve this problem, CT radiographic devices generally have a function that provides a preview of a CT image after the CT scanning to determine the need to repeat a radiograph based on the quality of the displayed CT image.

The determination is made by, for example, the operator's eye, a CT scan device that automatically determines based on the CT image quality, or both. In addition, an operator may determine the adequacy of the preset parameters based on the quality of the CT preview image. If the operator determines that the parameters are inadequate, the operator re-radiographs the subject after adjusting the parameters, as is disclosed in Japanese Patent Laid-Open No. 2002-365239.

However, in the methods in which the need to repeat a radiograph is determined based on the CT image created by CT reconstruction, the time required for the CT reconstruction delays the determination of the need to repeat a radiograph, and therefore, degrades the throughput of the CT inspection.

Additionally, the method in which an operator determines the need to repeat a radiograph by eye has drawbacks in that the criterion for the determination is not clear and the operator must make a complicated decision. These drawbacks also degrade the throughput of the CT inspection.

SUMMARY OF THE INVENTION

It is an object of the present invention to provide a radiation image processing apparatus, a radiation image processing method, a program, and a computer-readable medium that reduce the effect of a body-movement of a subject to be inspected.

In order to achieve the above object, for example, a radiation image processing apparatus of the present invention comprises the following arrangement. That is, the radiation image processing apparatus for reconstructing a CT image from a plurality of image data items of a subject to be inspected, taken from different angles, includes body-movement-information extracting means for extracting a structure constituting the subject from at least two image data items and obtaining at least one change indicating the body-movement of the subject based on the structure, repeat-radiograph determination means for determining whether or not a repeat radiograph is executed based on the at least one change, and CT reconstruction means for reconstructing a CT image from the plurality of image data items.

In order to achieve the above object, for example, a radiation image processing method of the present invention comprises the following arrangement. That is, the radiation image processing method for reconstructing a CT image from a plurality of image data items includes a step of extracting a structure constituting a subject to be inspected from at least two image data items and obtaining at least one change indicating the body-movement of the subject based on the information, a step of determining whether or not a repeat radiograph is executed based on the at least one change calculated in the extracting step, and a step of reconstructing a CT image from the plurality of image data items.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE PREFERRED EMBODIMENTS

Preferred embodiments of the present invention will now be described in detail in accordance with the accompanying drawings.

First Embodiment

Figure 1:
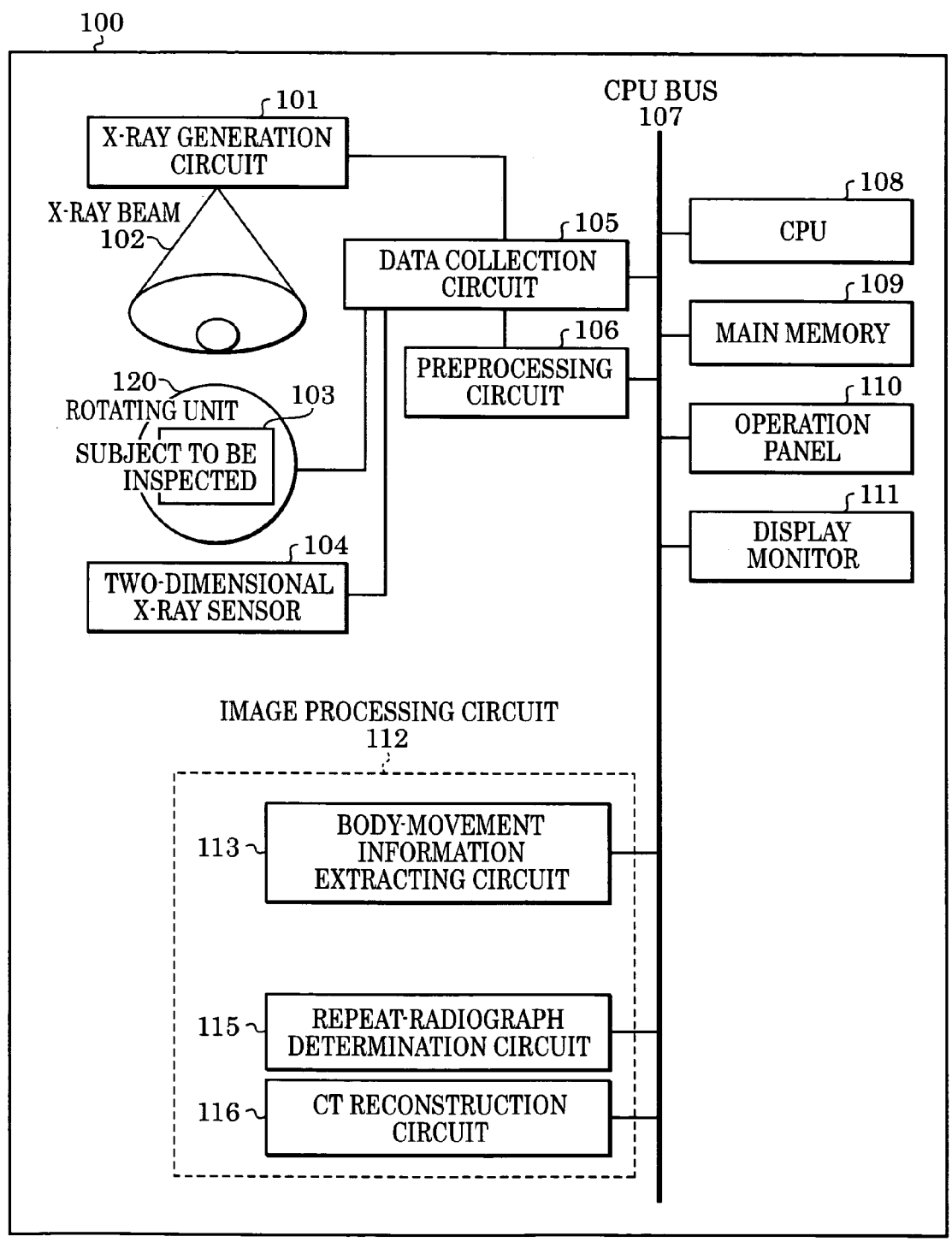
FIG. 1 is a block diagram of a first embodiment of the present invention.

FIG. 1 is a block diagram of a CT radiographic apparatus 100 according to a first embodiment of the present invention. That is, the CT radiographic apparatus 100 has a function to determine the need to repeat a radiograph. The CT radiographic apparatus 100 includes a preprocessing circuit 106, a CPU 108, a main memory 109, an operation panel 110, a display monitor 111, and an image processing circuit 112, all of which are connected to a CPU bus 107 to transfer data to each other.

Figure 2:
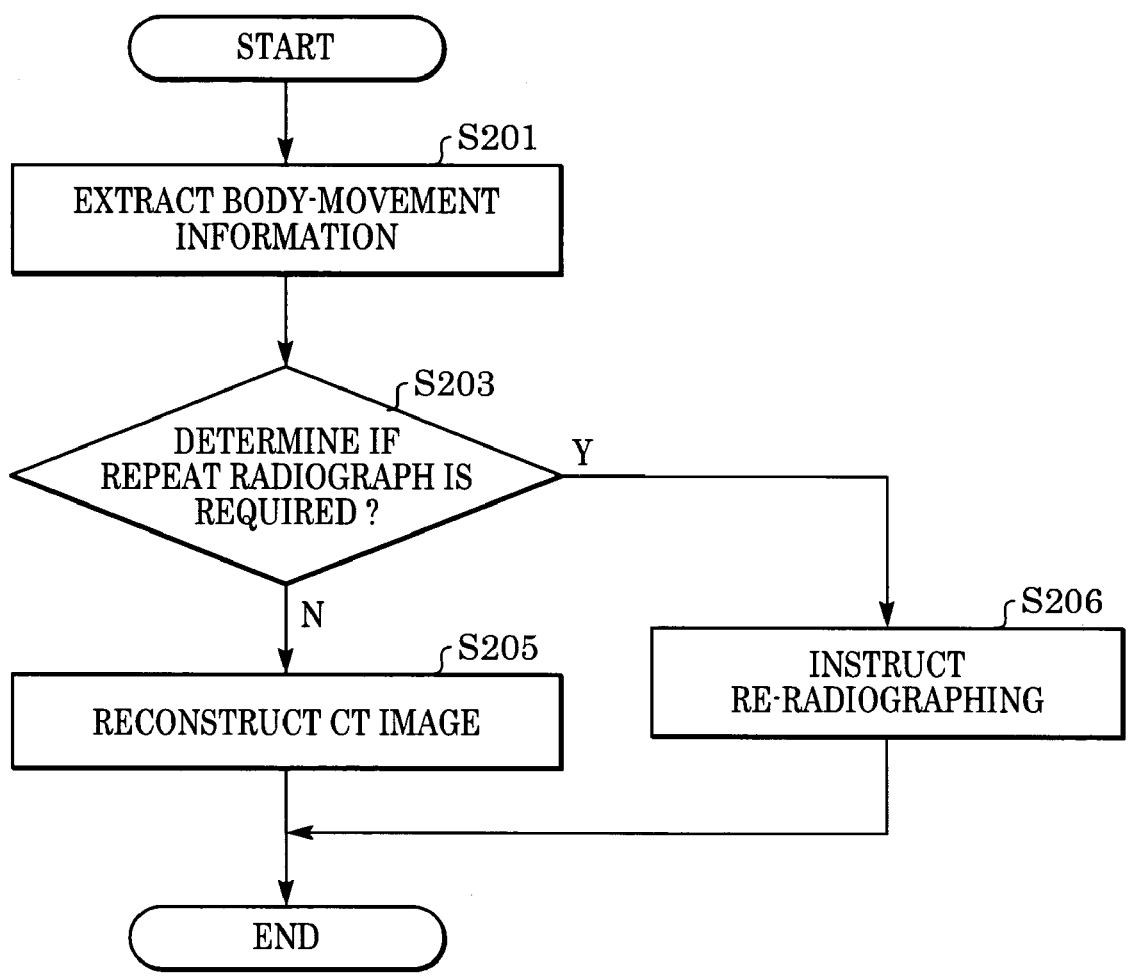
FIG. 2 is a flow chart of the process of an image processing circuit according to the first embodiment.

Additionally, the CT radiographic apparatus 100 includes a data collection circuit 105 connected to the preprocessing circuit 106, an X-ray generation circuit 101, a rotating unit 120, and a two-dimensional X-ray sensor 104, all of which are connected to the data collection circuit 105. The data collection circuit 105 is also connected to the CPU bus 107. FIG. 2 is a flow chart of the process of the image processing circuit 112 according to the first embodiment.

In CT radiographic apparatus 100, the main memory 109 stores various types of data required for processing by the CPU 108. Part of the main memory 109 is used as a working memory of the CPU 108.

The CPU 108 controls the operation of the entire CT radiographic apparatus 100 using the main memory 109 in response to operations from the operation panel 110. The operation of the CT radiographic apparatus 100 will be described below.

Herein, a program following a flow chart shown in FIG. 2 is stored in the main memory 109 or a ROM (not shown). The CPU 108 reads the program from the main memory 109 or the ROM and executes it.

First, the rotating unit 120 starts operating to rotate a subject 103 to be inspected. The X-ray generation circuit 101 then emits an X-ray beam 102 to the subject 103.

The X-ray beam 102 emitted from the X-ray generation circuit 101 propagates through the subject 103 while being attenuated, and reaches the two-dimensional X-ray sensor 104, which outputs a projection image. Herein, the projection image output from the two-dimensional X-ray sensor 104 is, for example, an image of part of the human body, such as a chest image.

The data collection circuit 105 converts the projection image output from the two-dimensional X-ray sensor 104 to an electrical signal, which is delivered to the preprocessing circuit 106. The preprocessing circuit 106 pre-processes the signal (projection image signal) from the data collection circuit 105 to adjust the offset and gain of the signal. The projection image signal pre-processed by the preprocessing circuit 106 is transferred, as a projection image, to the main memory 109 and the image processing circuit 112 via the CPU bus 107 under the control of the CPU 108. In this embodiment, the two-dimensional X-ray sensor 104, the data collection circuit 105, and the preprocessing circuit 106 are disposed separately. However, the two-dimensional X-ray sensor 104, the data collection circuit 105, and the preprocessing circuit 106 may be integrated into one unit as a sensor unit (not shown).

The CPU 108 directs the rotating unit 120 to rotate the subject 103, and controls the X-ray generation circuit 101 to emit the X-ray beam 102 continuously or discontinuously. During this operation (CT scanning), the two-dimensional X-ray sensor 104 sequentially captures projection images and sequentially delivers them to the data collection circuit 105. For example, while the subject 103 rotates 360 degrees, 512 pictures of the projection image are delivered to the data collection circuit 105. Thereafter, the data collection circuit 105 delivers the image data to the preprocessing circuit 106. The preprocessing circuit 106 performs the above-described process and then delivers the projection image data to the image processing circuit 112 and/or the main memory 109. By the above-described radiographic operation, projection images captured in different directions are sequentially transferred to the image processing circuit 112. At the same time, the projection images are delivered to the main memory 109 and stored.

The image processing circuit 112 (shown as a block 112 in FIG. 1) includes a body-movement information extracting circuit 113 that extracts information from a plurality of projection images in terms of a body movement of a subject to be inspected during CT scanning, a repeat-radiograph determination circuit 115 that determines the need to repeat a radiograph, and a CT reconstruction circuit 116 that reconstructs a CT image from a plurality of projection images. As used herein, the term body movement refers to any movement of a subject to be inspected. For example, the body movement includes a change in position of the diaphragm caused by the subject taking breaths and a change in position of the subject itself caused by a movement of the subject during CT scanning. If a body movement occurs during CT scanning, a CT image cannot be accurately reconstructed, which is a problem.

Figures 3, 4:
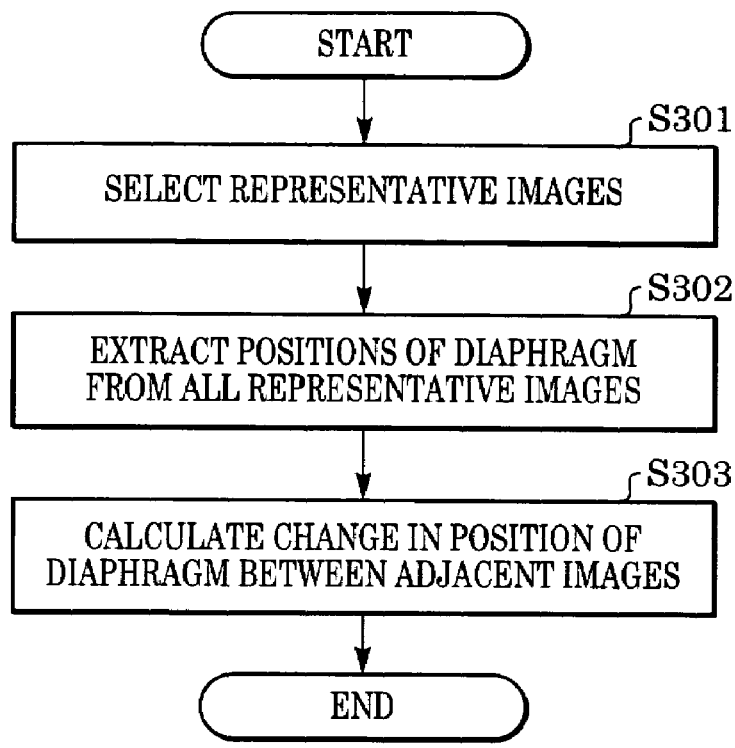
FIG. 3 is a flow chart of the process of a body-movement information extracting circuit according to the first embodiment.
FIG. 4 is a diagram showing body-movement information according to the first embodiment.
Figure 5:
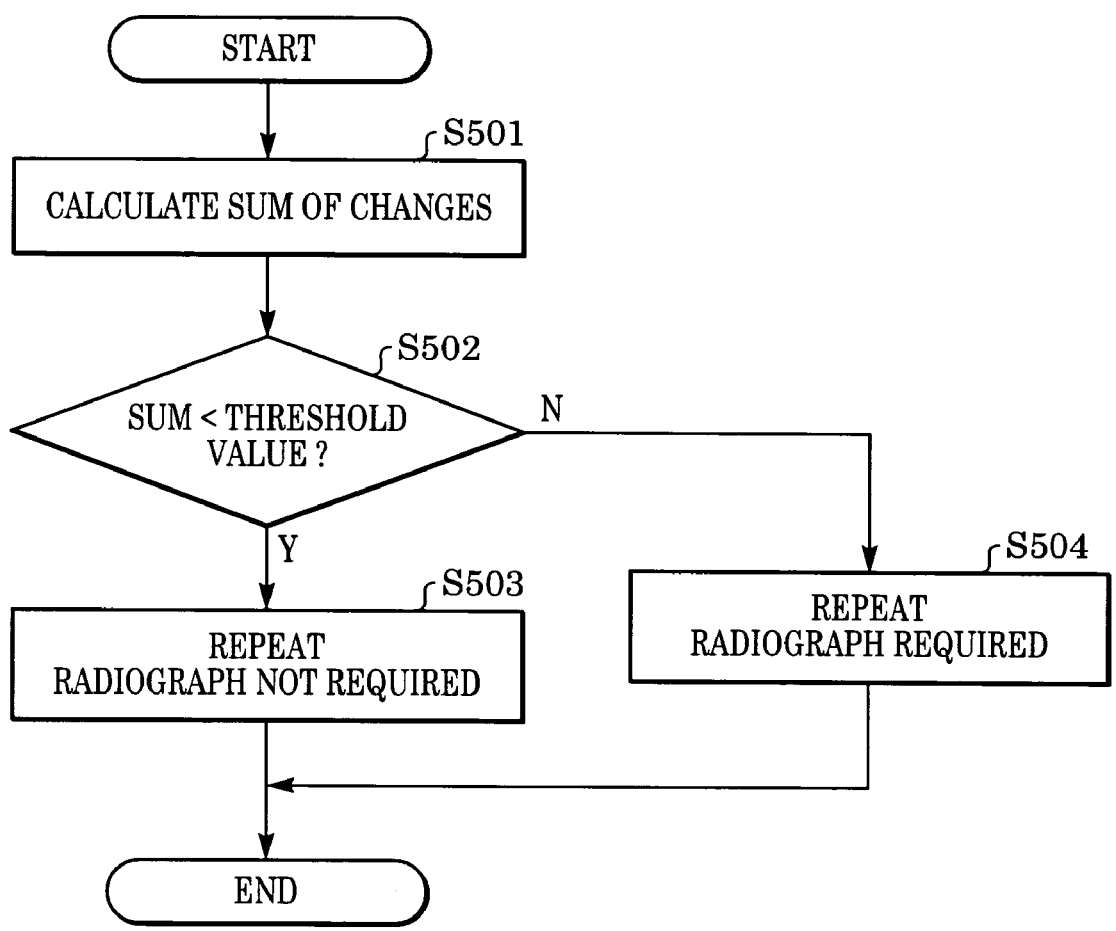
FIG. 5 is a flow diagram of the process of a repeat-radiograph determination circuit according to the first embodiment.
Figure 6:
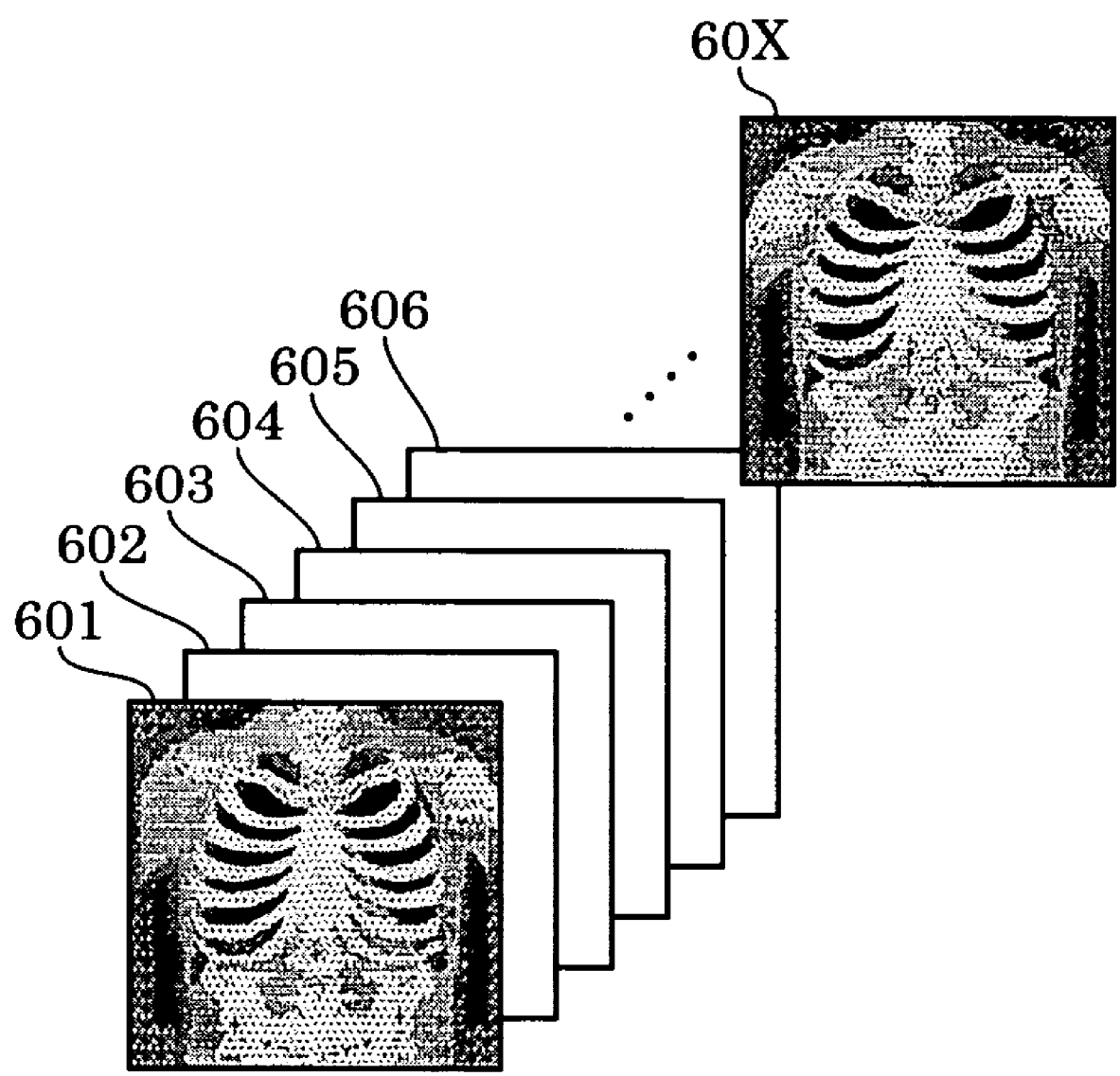
FIG. 6 shows projection images according to the first embodiment.
Figure 7:
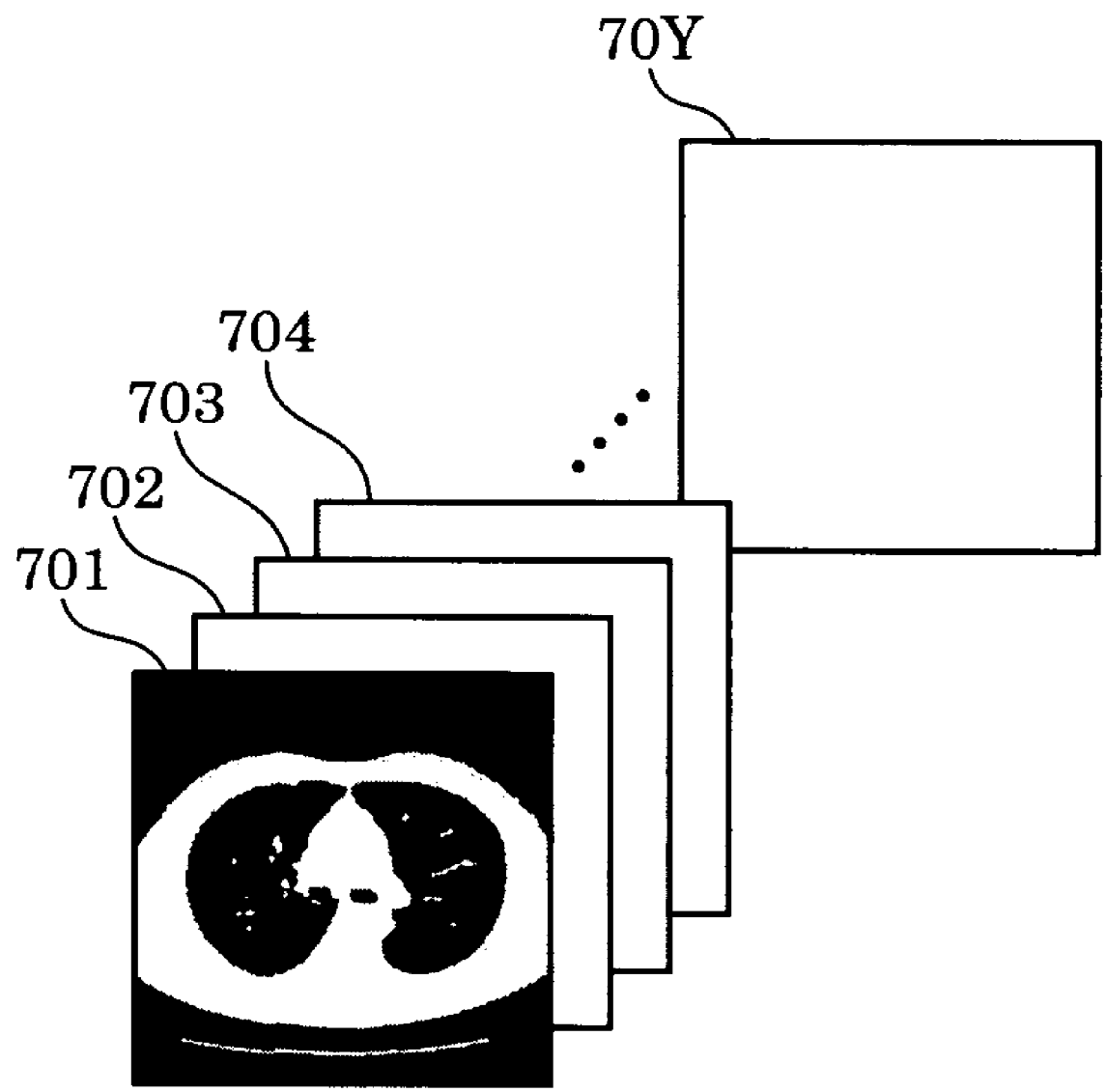
FIG. 7 shows CT images according to the first embodiment.

FIG. 3 is a flow chart of the process of the body-movement information extracting circuit 113. FIG. 4 shows an example of body-movement information output from the body-movement information extracting circuit 113. "Image No." refers to a number indicating a property assigned to a projection image. "Change" refers to the amount of body movement, which is calculated based on information of a subject to be inspected in projection images. FIG. 5 is a flow diagram of the process of the repeat-radiograph determination circuit 115. FIG. 6 shows projection images 601 to 60X taken from different angles. FIG. 7 shows CT images 701 to 70Y reconstructed from the projection images.

The operation of the image processing circuit 112 will be described next with reference to FIG. 2. The image processing circuit 112 sequentially receives, via the CPU bus 107, the plurality of projection images 601 to 60X processed by the preprocessing circuit 106 under the control of the CPU 108. By using the body-movement information extracting circuit 113, the image processing circuit 112 extracts body-movement information of a subject to be inspected during CT scanning (step S201). Subsequently, the repeat-radiograph determination circuit 115 determines whether or not a repeat radiograph is required (step S203). If, at step S203, it is determined that a repeat radiograph is not necessary, the CT reconstruction circuit 116 reconstructs the CT images 701 to 70Y from the projection images 601 to 60X (step S205). If it is determined that a repeat radiograph is necessary, the image processing circuit 112 instructs re-radiographing (step S206) and the process is completed.

The operation of the body-movement information extracting circuit 113 at step S201 will be described next with reference to FIG. 3. To pass images to a subsequent process, the body-movement information extracting circuit 113 selects at least two representative images among the plurality of projection images 601 to 60X received (step S301).

The method for selecting the representative images includes, but is not limited to, a technique to select every Kth image, where K is a predetermined constant, and a technique to select two images, the first input image and the last input image. Alternatively, all the input images may be selected as representative images. In this embodiment, this method is used hereinafter.

Thereafter, the body-movement information extracting circuit 113 extracts at least one structure, which is part of the subject, from the selected representative images. In this embodiment, the subject is a chest of the human body and a diaphragm is extracted as the structure (step S302). To extract a particular structure from the subject, an anatomical method of analysis is widely used. For example, Japanese Patent Laid-Open No. 11-151232 discloses a method in which a binary image processed using a threshold value is labeled and, among the labeled areas, areas that are smaller than a predetermined area and predetermined areas in contact with the upper, lower, right, and left edges of the input image are excluded to extract a lung area. In addition, SPIE Medical Imaging 97, "Automatic Segmentation of Anatomic Regions in Chest Radiographs using an Adaptive-Sized Hybrid Neural Network" discloses a method in which a structure is segmented by using a neural network that is trained through features including optical density and anatomical address information of each pixel, and entropy information in the vicinity of each pixel. In this embodiment, a lung area is first extracted by using one of these methods, and then the diaphragm is extracted while considering the installation conditions of the two-dimensional X-ray sensor 104. More specifically, if the two-dimensional X-ray sensor 104 is disposed such that the longitudinal direction of the subject is identical to the longitudinal direction of the sensor, the diaphragm in a human-chest image must be positioned in the lower section of the received image. Accordingly, the diaphragm can be extracted by using this condition and the above-described lung area.

Subsequently, changes in position of the diaphragm are calculated based on the positions of the diaphragm in the representative images. For example, the representative images are lined up in order of captured time. The absolute value of a difference between coordinates of the diaphragm in adjacent representative images along the body-axis direction (the vertical direction of projection images in FIG. 6) is calculated as a change in position of the diaphragm for the corresponding representative image (step S303). More specifically, the outline of a lower edge of a diaphragm in one of the representative images is extracted, and the outline of a lower edge of a diaphragm in the neighboring representative image is extracted. The neighboring representative image is an image immediately before or after the above-described image, and is, in general, an image of the subject taken from a different shot angle from that of the above-described image. Subsequently, the lengths of both outlines are normalized to a predetermined width in the horizontal direction, namely, the direction perpendicular to the body-axis direction. Herein, a first normalized outline is represented as f1(x, y) and a second normalized outline is represented as f2(x, y), where (x, y) are coordinates. In this case, the change is represented by the following equation (1). The width of the normalized outline is W. That is, the x coordinate of the outlines ranges from 0 to W. As used herein, coordinates (x, y) in the normalized outlines are referred to as normalized coordinates.

[Formula 1]

$$H = \left(\int_0^w |f1(x, y) - f2(x, y)| dx\right) / W \quad (1)$$

Additionally, since a heart area that continuously moves exhibits a high change value, the heart area is excluded from the diaphragm area. To extract the heart area, the anatomical method of analysis is used, as in the extraction of the diaphragm area. After the body-movement information extracting circuit 113 calculates all the changes in position of the diaphragm in the representative images and outputs body movement information shown in FIG. 4, the operation of the body-movement information extracting circuit 113 is completed.

According to equation (1), a change is calculated based on information from two images. However, the change may be calculated based on information from three or more images. In this case, the change may be calculated according to, for example, the following equation (2). In equation (2), f0(x, y) is a normalized outline which is extracted from a neighboring image different from the neighboring image from which f2(x, y) is extracted.

[Formula 2]

$$H = \left(\int_0^w (|f1(x, y) - f2(x, y)| + |f1(x, y) - f0(x, y)|) dx\right) / W \quad (2)$$

Additionally, the method for extracting a body movement is not limited to the above-described method. For example, after diaphragm regions are extracted from a target image and its neighboring image, overlap areas of the extracted diaphragm regions may be defined as a change value. In this case, as the following equation (3) indicates, an area where the extracted diaphragm regions do not overlap is divided by an area of the diaphragm region in a representative image. The resultant value is used as a change value.

[Formula 3]

$$H = \left(\int_0^d \int_0^d |f1(x, y) - f2(x, y)| dx dy\right) / S \quad (3)$$

where f1(x, y) and f2(x, y) represent binary images in which a pixel inside the structure is "1" and a pixel outside the structure is "0". S represents an area of the structure f1(x, y).

In the above-described example, a diaphragm is extracted. However, a body movement can be detected by obtaining an outline or overlap area of a lung area in the same manner. As described above, a change in position that indicates a body movement can be calculated from information of a structure that is part of a subject. Also, the whole subject may be used as the structure, as will be described below in another embodiment.

The operation of the repeat-radiograph determination circuit 115 at step S203 will be described next with reference to FIG. 5. The repeat-radiograph determination circuit 115 determines whether or not a repeat radiograph is required based on a received change, namely, a change in position of a diaphragm in each representative image in this embodiment. Firstly, the repeat-radiograph determination circuit 115 calculates the sum of the changes in position of the diaphragm in the representative images (step S501). Then, the sum is compared to a predetermined threshold value (step S502). If the sum is smaller than the threshold value, it is determined that a repeat radiograph is not required (step S503). Otherwise, it is determined that a repeat radiograph is required (step S504). Thereafter, the operation of the repeat-radiograph determination circuit 115 is completed.

The sum may be calculated by the body-movement information extracting circuit 113 and may be used as the change in position. In this case, the repeat-radiograph determination circuit 115 can determine whether or not a repeat radiograph is required by comparing the received change with the predetermined value. The type of the change is not limited to one type. The determination may be made based on a plurality of change types. For example, both a change in position of a diaphragm and a change in position of a lung area may be used at the same time. In this case, each change is compared with a predetermined threshold value. If both changes are greater than the predetermined threshold value, it is determined that a repeat radiograph is required. Alternatively, if either one of the changes is greater than the predetermined threshold value, it is determined that a repeat radiograph is required. Use of a plurality of types of changes increases the accuracy of the determination.

Finally, if, at step S203, it is determined that a repeat radiograph is not required, the CT reconstruction circuit 116 reconstructs a CT image at the above-described step S205. Since techniques for generating CT images from projection images using CT reconstruction are well known, a description of the technique is not included herein.

In the above-described embodiment, although a change in position is calculated during radiographing, the change may be calculated in the same manner using projection images stored in the main memory 109. In addition, although the subject 103 is rotated in this embodiment, rotating the X-ray generation circuit 101 and the two-dimensional X-ray sensor 104, of course, provides the same advantage.

According to the first embodiment of the present invention, since the need to repeat a radiograph is determined using projection images, CT reconstruction time, which the known methods require to determine the need to repeat a radiograph, is completely eliminated, thus increasing the throughput of the CT inspection. Additionally, the determination to repeat a radiograph can be made based on a clear criterion. Furthermore, the determination can be automatically made, thus decreasing the workload of the operator.

Second Embodiment

Figure 8:
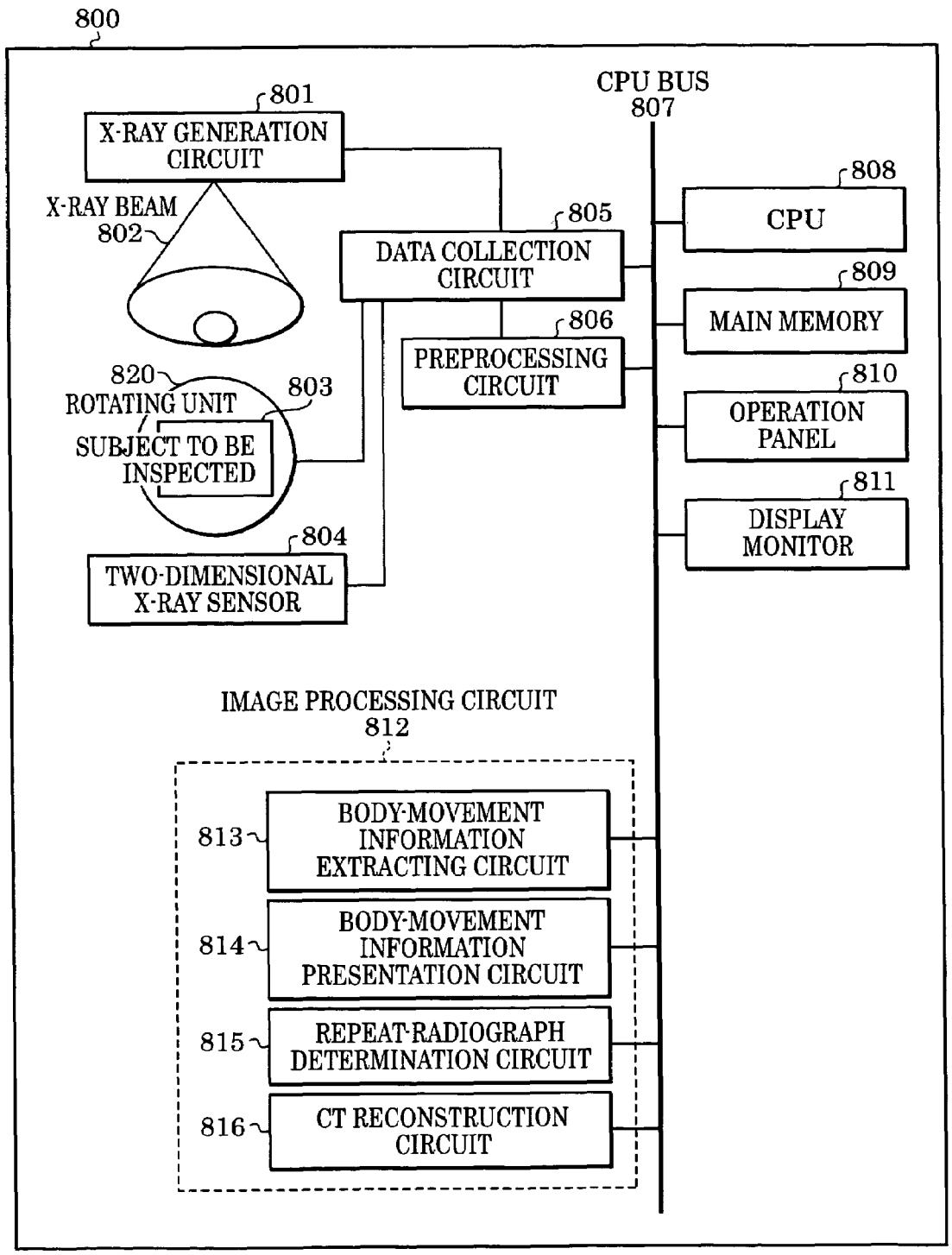
FIG. 8 is a block diagram of a second embodiment of the present invention.

FIG. 8 is a block diagram of the CT radiographic apparatus 800 according to a second embodiment of the present invention. The difference between the CT radiographic apparatus 800 and the CT radiographic apparatus 100 described in the first embodiment is that a body-movement information presentation circuit 814 is added to an image processing circuit 812. Accordingly, only the body-movement information presentation circuit 814 and parts associated with it will be described below. The other elements of CT radiographic apparatus 800 correspond to similar elements of CT radiographic apparatus 100, depicted in FIG. 1.

As in the first embodiment, operations from emission of an X-ray beam to transmission of projection images are repeated while a rotating unit 820 operates. The projection images taken from different angles are sequentially transferred to the image processing circuit 812.

The image processing circuit 812 (shown as a block 812 in FIG. 8) includes the body-movement information presentation circuit 814 that presents body movement information on a display monitor 811, in addition to the same circuits shown in the first embodiment.

Figure 9:
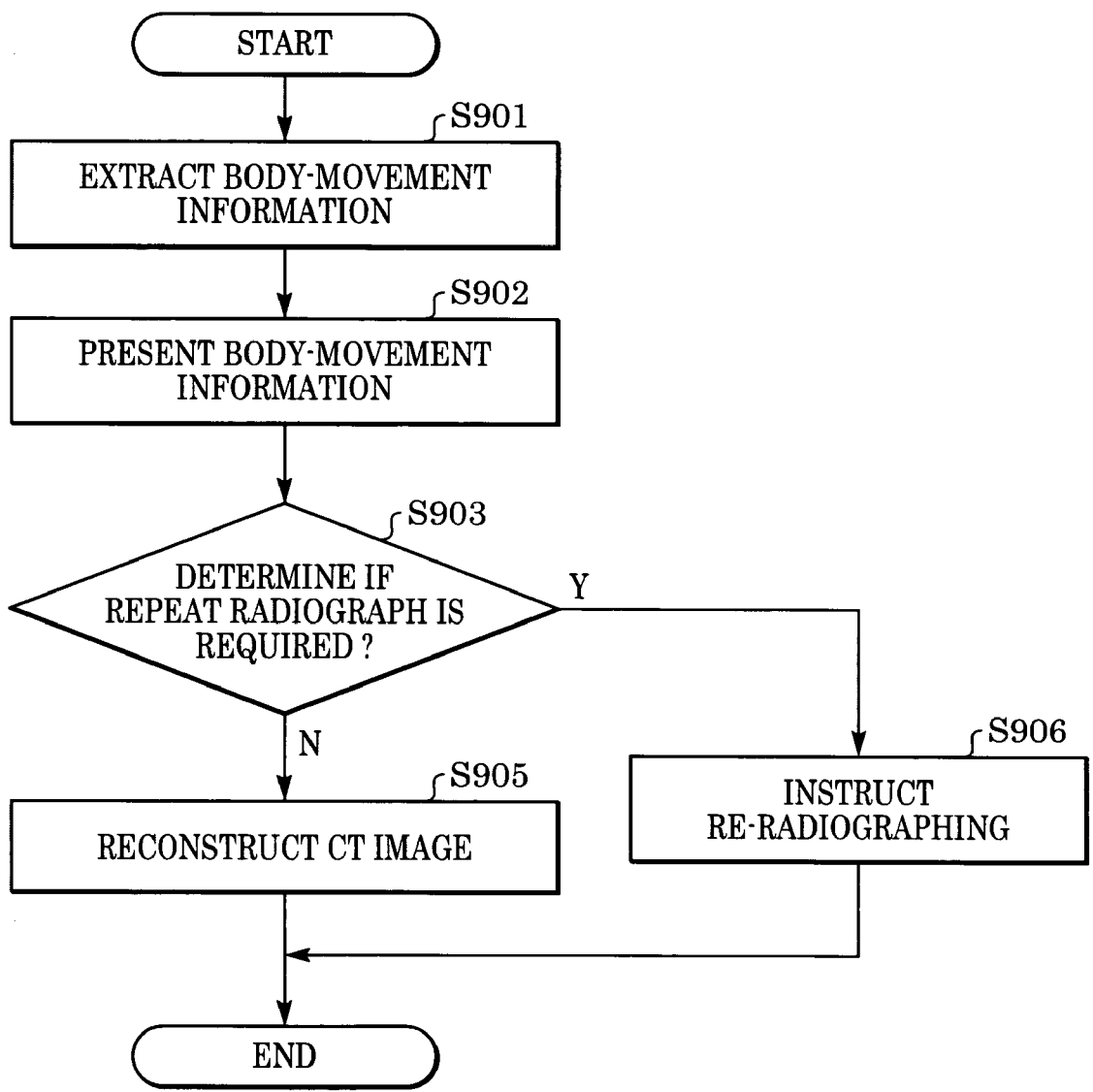
FIG. 9 is a flow chart of the process of an image processing circuit according to the second embodiment.
Figure 10:
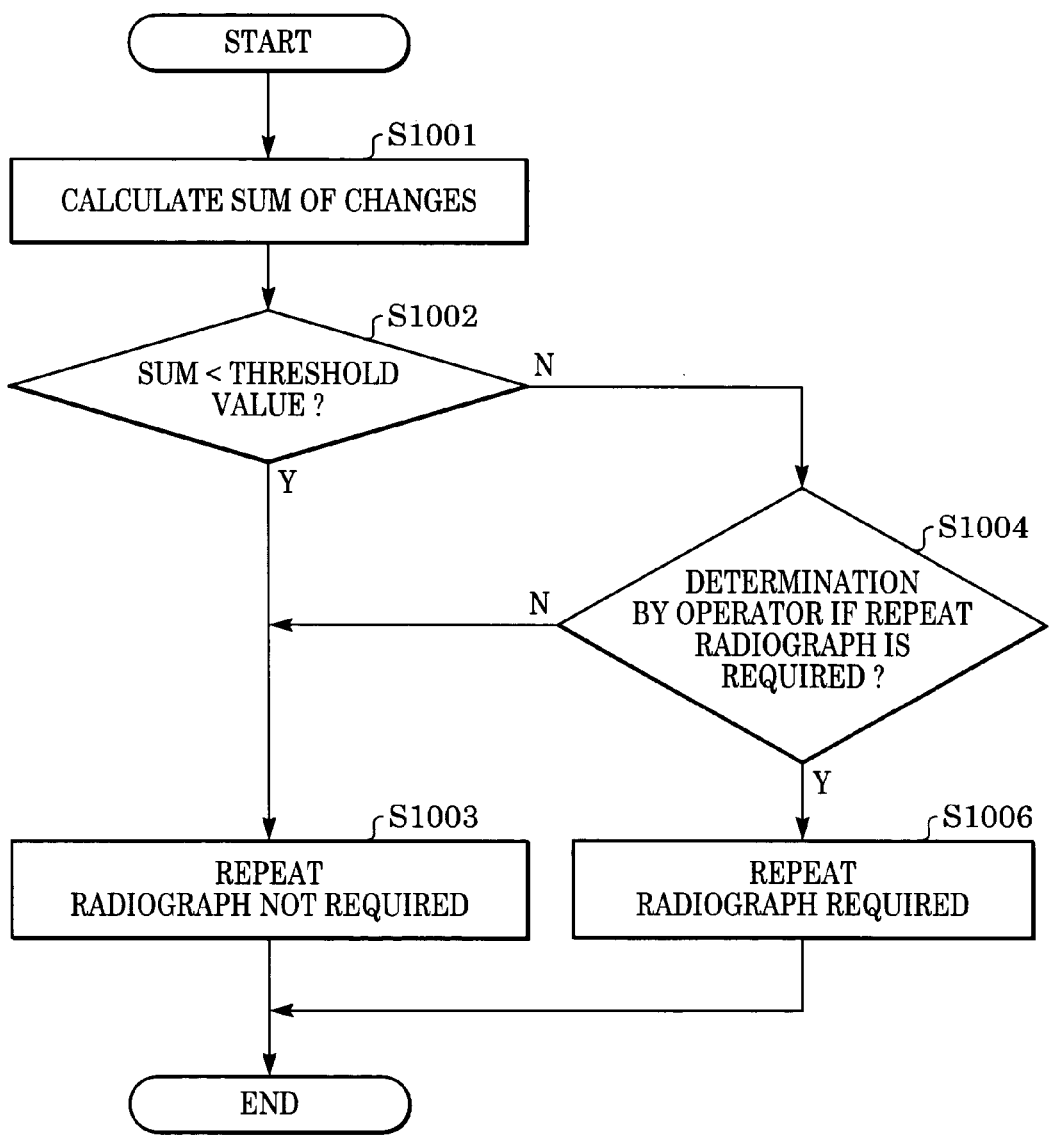
FIG. 10 is a flow diagram of the process of a repeat-radiograph determination circuit according to the second embodiment.

FIG. 9 is a flow diagram of a process of the image processing circuit 812 according to the second embodiment. FIG. 10 is a flow diagram of a process of a repeat-radiograph determination circuit 815.

The operation of the image processing circuit 812 will be described next with reference to FIG. 9.

As in the first embodiment, the image processing circuit 812 sequentially receives, via a CPU bus 807, the plurality of projection images 601 to 60X processed by a preprocessing circuit 806 under the control of a CPU 808. By using a body-movement information extracting circuit 813, the image processing circuit 812 extracts body-movement information of a subject to be inspected during CT scanning (step S901). Subsequently, the body-movement information presentation circuit 814 displays all the body movement information, some of the body movement information of the subject, or statistics of the information on a display monitor 811 (step S902). The repeat-radiograph determination circuit 815 then determines whether or not a repeat radiograph is required based on the body movement information and an operator's decision (step S903). If, at step S903, it is determined that a repeat radiograph is not necessary, a CT reconstruction circuit 816 reconstructs CT images 701 to 70Y from the projection images 601 to 60X (step S905). If it is determined that a repeat radiograph is necessary, the image processing circuit 812 instructs re-radiographing (step S906) and the process is completed.

Since the operation of the body-movement information extracting circuit 813 at step S901 is the same as that at step S201 described in the first embodiment, a description is not included herein. The body movement information output from the body-movement information extracting circuit 813 is delivered to the body-movement information presentation circuit 814 and the repeat-radiograph determination circuit 815.

The process at step S902 will be described next. The body-movement information presentation circuit 814 displays the received body-movement information on the display monitor 811. For example, all the information may be displayed in the form of a list, or only items that satisfy a predetermined criterion may be extracted and displayed. Alternatively, statistics calculated by using statistical techniques may be presented. In this embodiment, a sum of changes in position of the diaphragm is presented.

The operation of the repeat-radiograph determination circuit 815 at step S903 will be described next with reference to FIG. 10. The repeat-radiograph determination circuit 815 determines whether or not a repeat radiograph is required based on a received change, namely, a change in position of the diaphragm in each representative image in this embodiment, and a decision of an operator who receives the presentation of the body-movement information. Firstly, the repeat-radiograph determination circuit 815 calculates a sum of changes in position of the diaphragm in the representative images (step S1001). Then, the sum is compared to a predetermined threshold value (step S1002). If the sum is smaller than the threshold value, it is determined that a repeat radiograph is not required (step S1003) and the process is completed. Otherwise, the operator determines whether or not a repeat radiograph is required based on the presented body-movement information (step S1004), and a repeat radiograph is determined or not determined (step S1003 or step S1006). Thereafter, the operation of the repeat-radiograph determination circuit 815 is completed.

Finally, if, at step S903, it is determined that a repeat radiograph is not required, the CT reconstruction circuit 816 reconstructs a CT image at the above-described step S905. Since techniques for generating CT images from projection images using CT reconstruction are well known, a description of the techniques is not included herein.

According to the second embodiment, since the need for a repeat radiograph is determined using projection images, CT reconstruction time, which the known methods require to determine the need for a repeat radiograph, is completely eliminated, thus increasing the throughput of the CT inspection. Additionally, the determination of a repeat radiograph can be made based on a clear criterion. Furthermore, since intuitive and user-friendly body-movement information is presented to an operator, the operator can easily determine whether or not a repeat radiograph is required. Furthermore, the operator can describe the cause of a previous error to a patient and can advice measures to avoid the error to the patient. As a result, the number of repeat radiographs is reduced, thus increasing the throughput of the CT inspection.

Third Embodiment

In a third embodiment of the present invention, a CT radiographic apparatus having the same configuration as that of the CT radiographic apparatus 100 in the first embodiment is used. In this embodiment, only the processes of the body-movement information extracting circuit 113 and the repeat-radiograph determination circuit 115 in the image processing circuit 112 are different from those in the first embodiment. Accordingly, only the differences will be described below.

As in the first embodiment, operations from emission of an X-ray beam 102 to transmission of projection images are repeated while the rotating unit 120 operates. The projection images taken from different angles are sequentially transferred to the image processing circuit 112.

Figure 11:
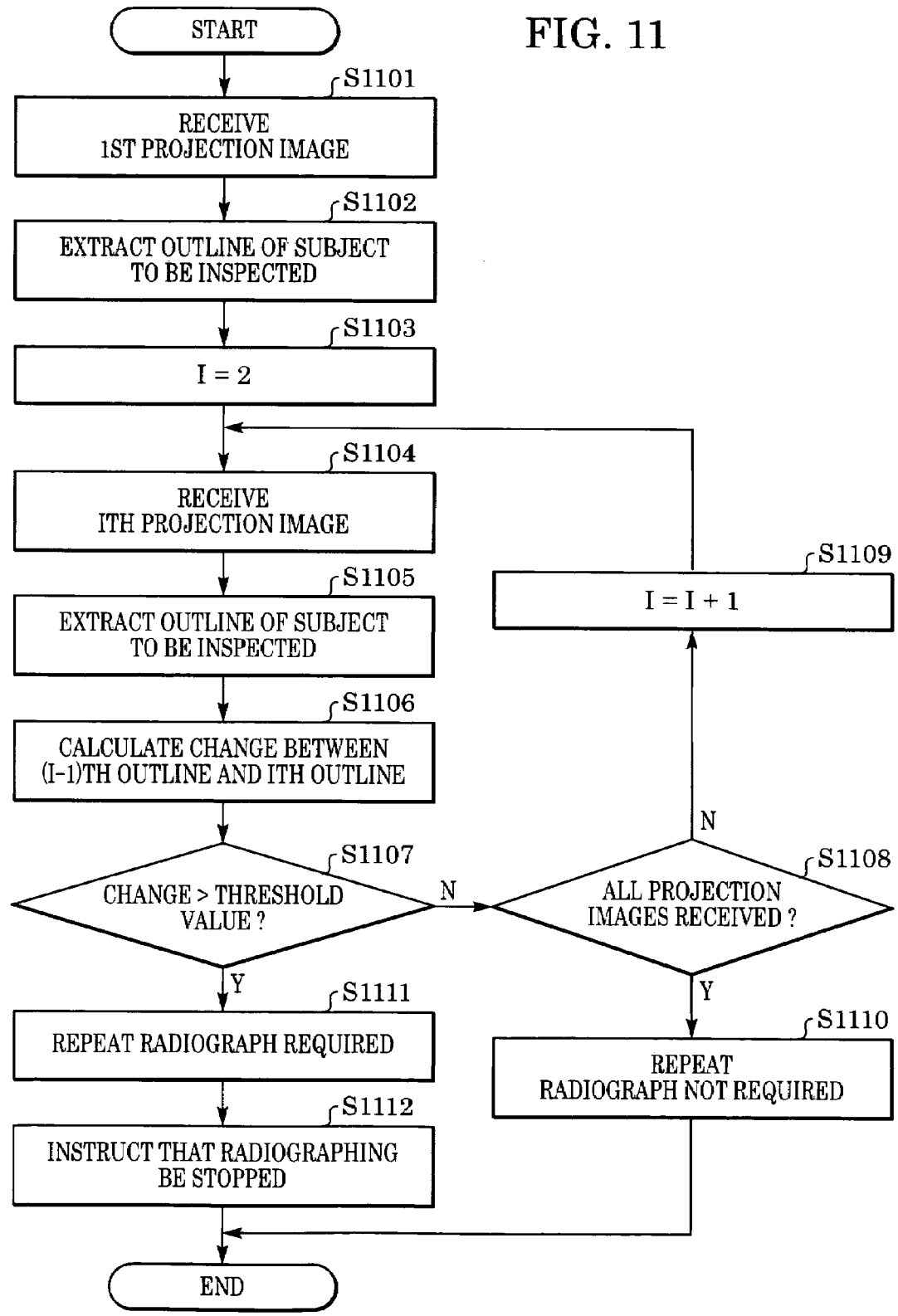
FIG. 11 is a flow diagram of the processes of a body-movement information extracting circuit and a repeat-radiograph determination circuit according to a third embodiment of the present invention.

The image processing circuit 112 sequentially receives projection images. By using the body-movement information extracting circuit 113, the image processing circuit 112 extracts body-movement information of a subject to be inspected during CT scanning (step S201). The repeat-radiograph determination circuit 115 then determines whether or not a repeat radiograph is required (step S203). These methods are different from those in the first embodiment and follow processes shown in FIG. 11.

Firstly, at steps S1101 to S1105, two projection images are received, and an outline of a subject is extracted from each image. Herein, any outline extraction method may be used. In general, since an X-ray beam 102 is significantly attenuated after it penetrates a subject to be inspected 103, such as a human body, the X-ray beam 102 creates an edge having a large difference of pixel value in the vicinity of an outline of the subject in a projection image. Therefore, the outline can be accurately extracted by using various types of basic edge-extraction algorithms.

Figure 12:
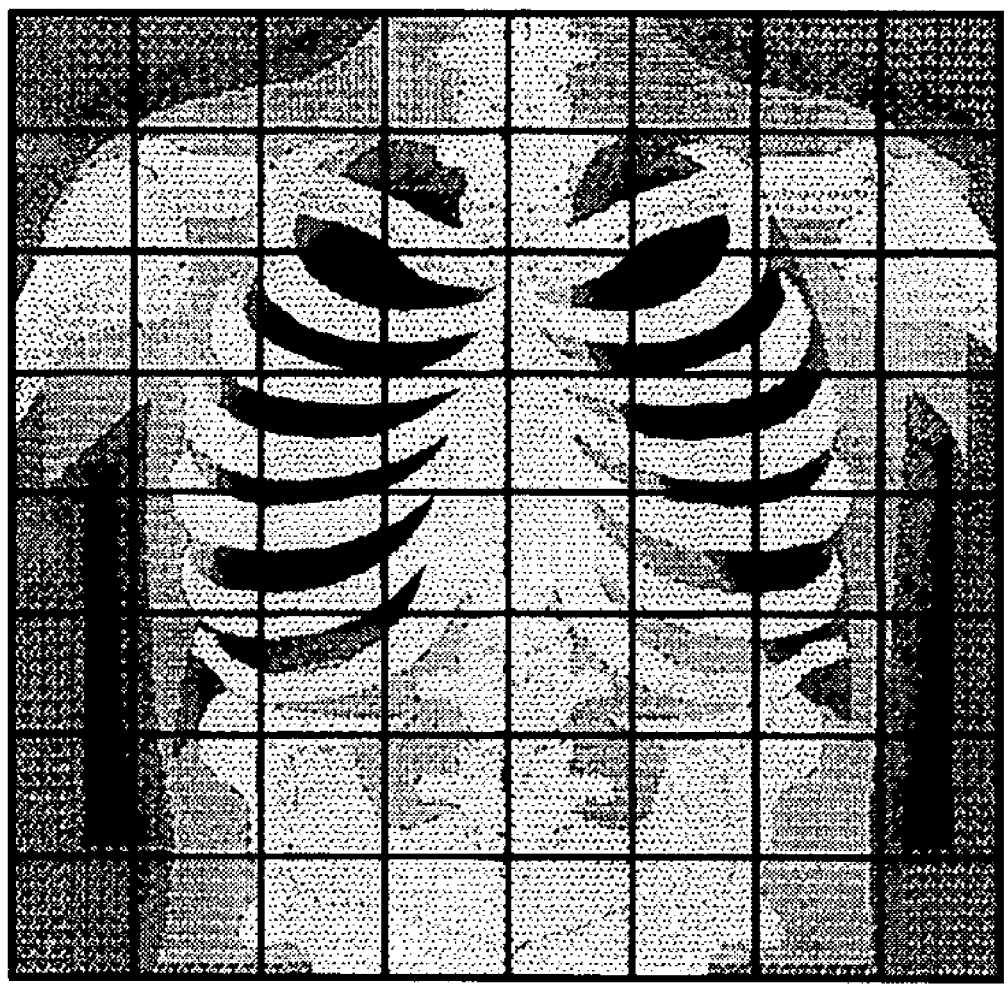
FIG. 12 shows blocks used to calculate a change between outlines according to the third embodiment.

Subsequently, a change in position between the outlines extracted at steps S1102 and S1105 is calculated (step S1106). In this embodiment, as shown in FIG. 12, a projection image is divided into N-by-N blocks (for example, 8-by-8 blocks). An amount of movement is calculated by a position alignment process only for a block from which the outline is extracted. The amounts of movement are added and defined as a change in position of the outline between the projection images. Since the (I−1)th projection image and the Ith projection image are taken from different angles, a change in position of the outline is not necessarily zero even though the subject does not move at all. However, in general, since thousands of projection images are taken per rotation during CT scanning, a change in position of the outline between two adjacent images should be extremely small if the subject does not move.

Thereafter, it is determined whether the change in position of the outline calculated at step S1106 exceeds a predetermined threshold value (step S1107). To find an appropriate threshold value, a change in position of the outline is obtained in advance in the case of a completely stationary subject, such as a human body phantom. In this embodiment, 120% of the change that is calculated using a human body phantom is used as the threshold value.

If the change in position of outline between the (I−1)th projection image and the Ith projection image does not exceed the threshold value, the image processing circuit 112 receives the next projection image and the same process as described above is repeated (steps S1108 and S1109). If all the projection images are received and the change in position of outline between the (I−1)th projection image and the Ith projection image does not exceed the threshold value, it is determined, at step S1110, that a repeat radiograph is not required, and the process is completed.

If, however, the change in position of the outline between the (I−1)th projection image and the Ith projection image exceeds the threshold value, it is determined, at step S1111, that a repeat radiograph is required. The image processing circuit 112 instructs that the radiographing be immediately stopped (step S1112), and the process is completed.

This is the end of the processes of the body-movement information extracting circuit 113 and the repeat-radiograph determination circuit 115. Subsequent processes, steps S205 and S206, are the same as those in the first embodiment. Accordingly, descriptions thereof are not included herein.

As described above, according to the third embodiment, since the need to repeat a radiograph is determined using projection images, CT reconstruction time, which the known methods require to determine the need for a repeat radiograph, is completely eliminated, thus increasing the throughput of the CT inspection. Additionally, the determination of a repeat radiograph can be performed based on a clear criterion. Furthermore, since the determination of a repeat radiograph can be automatically made, the workload of the operator can be reduced. Furthermore, since the radiographing is stopped immediately after a body movement is detected, unnecessary exposure of the subject to radiation can be reduced.

Fourth Embodiment

In a fourth embodiment of the present invention, a CT radiographic apparatus having the same configuration as that of the CT radiographic apparatus 100 in the first embodiment is used. The difference between this embodiment and the first embodiment is that, when projection images are captured, the data collection circuit 105 receives angle information from the rotating unit 120 and sends the angle information to the image processing circuit 112 along with the captured projection images. Also, the processes of the body-movement information extracting circuit 113 and the repeat-radiograph determination circuit 115 in the image processing circuit 112 are different from those in the first embodiment. Accordingly, only these differences will be described below.

As in the first embodiment, operations from emission of an X-ray beam 102 to transmission of projection images are repeated while the rotating unit 120 operates. The projection images taken from different angles are sequentially transferred to the image processing circuit 112. At that moment, in this embodiment, the data collection circuit 105 receives angle information during a radiographic period from the rotating unit 120 and transmits the angle information and the corresponding projection image to the image processing circuit 112.

Figure 13:
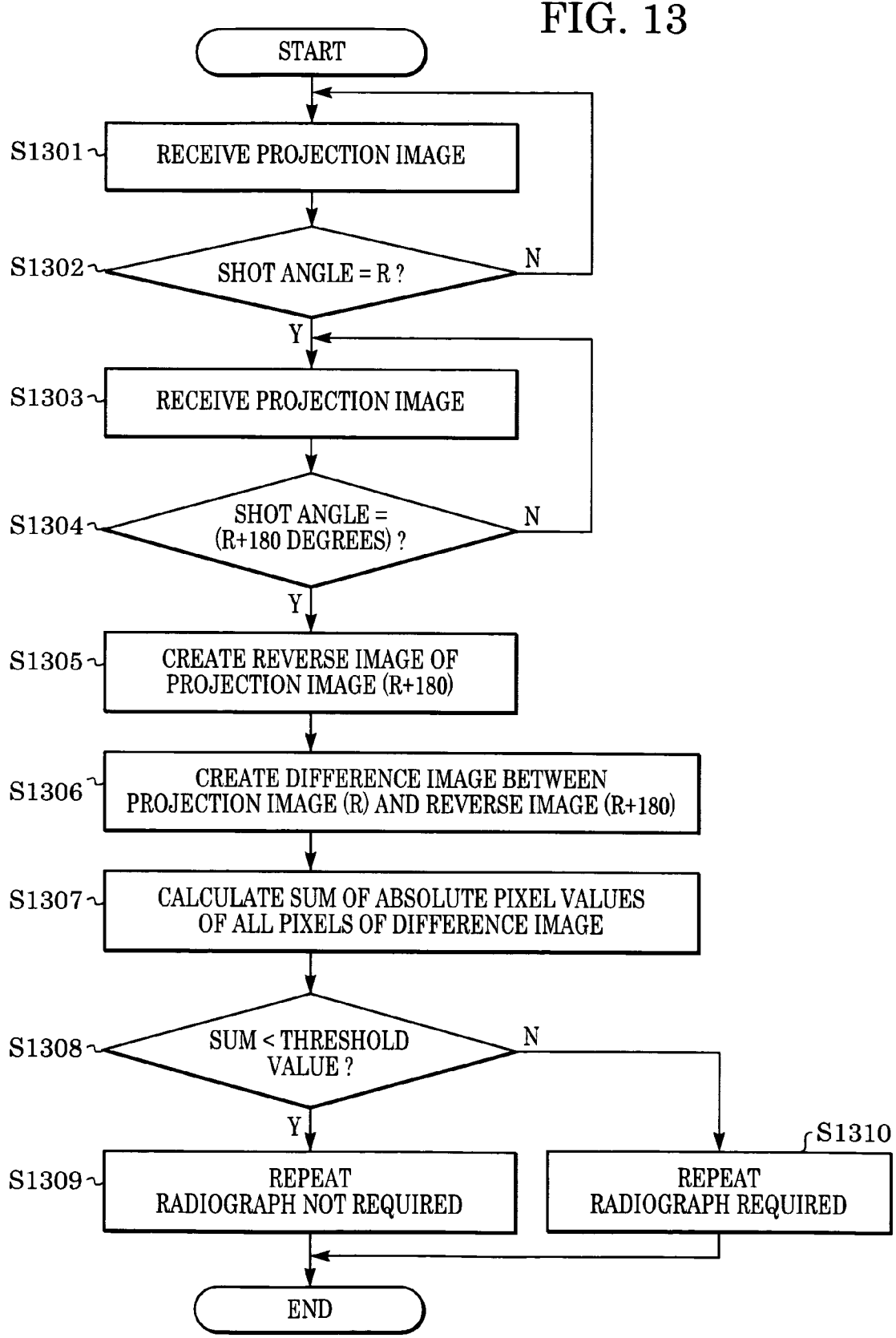
FIG. 13 is a flow diagram of the processes of a body-movement information extracting circuit and a repeat-radiograph determination circuit according to a fourth embodiment of the present invention.

The image processing circuit 112 sequentially receives the projection images and the corresponding angle information. By using the body-movement information extracting circuit 113, the image processing circuit 112 extracts body-movement information of a subject to be inspected during CT scanning (step S201). The repeat-radiograph determination circuit 115 then determines whether or not a repeat radiograph is required (step S203). These methods are different from those in the first embodiment and follow processes shown in FIG. 13.

Firstly, at steps S1301 and S1302, a reception process is repeated until a projection image taken at a shot angle of R (hereinafter referred to as a "projection image (R)") is received. In a further process, a projection image taken from a shot angle of R+180 degrees, that is, a projection image taken from the reverse angle to the projection image (R), is required. Accordingly, if a shot angle at radiograph start time is 0 degree, the value of R must be chosen so as to satisfy the inequality $0 \leq R \leq 180$ for a full-scan (radiographs are taken from 360 degrees, i.e., during one rotation), and $0 \leq R \leq$ fan-angle of X-ray projection for a half-scan (radiographs are taken from 180 degrees, i.e., during a half rotation). In this embodiment, for the sake of simplicity, the shot angle at radiograph start time is set to 0 degree and R is also set to 0 degree.

Subsequently, as in the above-described steps S1301 and S1302, a reception process is repeated until a projection image taken at an angle of R+180 degrees (hereinafter referred to as a "projection image (R+180)") is received (steps S1303 and S1304). Upon receipt of the projection image (R+180), at step S1305, a reverse image of the projection image (R+180) (hereinafter referred to as a "reverse image (R+180)") is created. In the reverse operation, pixels which are positioned symmetrically with respect to the rotational axis of the subject are interchanged. In this embodiment, a mirror reversed image is created.

Subsequently, a difference image between the projection image (R) and the reverse image (R+180) is created (step S1306). Absolute pixel values of all pixels of the difference image are added (step S1307). Under the assumption that X-ray beams incident on the X-ray sensor are exactly parallel, if the subject is completely stationary, this sum must be zero or extremely small even though some noise and various types of errors occur. The sum should be above a certain value only when the subject moves.

However, in an actual radiographic environment, since a distance between an X-ray sensor and an X-ray source is finite, the X-ray beams are not parallel over the entire surface of the X-ray sensor. In consideration of variation in output level of the X-ray beam and scattered radiation, the sum generally exhibits a certain value although the subject is stationary. Therefore, at step S1308, the sum is evaluated using some threshold value that is determined after considering these factors. To determine the predetermined threshold value, for example, a human body phantom is used, as in the third embodiment.

Additionally, at the above-described step S1307, a target region for the calculation in a projection image may be limited to an area at the center of the projection image in accordance with a distance between the X-ray sensor and the X-ray source. Since this is not a key point of the present invention, a detailed description is not included herein.

Finally, if, at step S1308, the sum does not exceed the threshold value, it is determined that a repeat radiograph is not required. If the sum exceeds the threshold value, it is determined that a repeat radiograph is required. The process is then completed.

This is the end of the process of the body-movement information extracting circuit 113 and the repeat-radiograph determination circuit 115 according to the fourth embodiment. Subsequent processes, steps S205 and S206, are the same as those in the first embodiment. Accordingly, descriptions thereof are not included herein.

As described above, according to the fourth embodiment, since the need for a repeat radiograph is determined using projection images, CT reconstruction time, which the known methods require to determine the need to repeat a radiograph, is completely eliminated, thus increasing the throughput of the CT inspection. Additionally, the need to repeat a radiograph can be determined based on a clear criterion. Furthermore, since the need for a repeat radiograph can be automatically determined, the workload of the operator can be reduced. Furthermore, since a body movement is determined by simple error-free processes, such as reverse image creation, difference image creation, and a thresholding process, the determination is advantageously reliable and accurate for various types of subjects. Also these simple processes advantageously decrease determination time and the load of the radiographic apparatus.

As described above, according to the present invention, a radiation image processing apparatus, a radiation image processing method, a program, and a computer-readable medium, all of which reduce the effect of a body movement, can be provided.

It will be appreciated that the object of the present invention is also achieved by providing a storage medium that stores software (a program) that achieves the functions of the apparatus or system described in the first embodiment to the fourth embodiment to the apparatus or system and by causing a computer (for example, a CPU or a MPU) to read and execute the program stored in the storage medium.

In this case, the program itself read from the storage medium achieves the functions described in the first embodiment to the fourth embodiment. A storage medium that stores the program and the program itself achieve the present invention.

The storage medium that provides the program includes a ROM, a floppy (trademark) disk, a hard disk, an optical disk, a magneto optical disk, a CD-ROM, a CD-R, a magnetic tape, and a nonvolatile memory card.

It will be appreciated that embodiments of the present invention include not only the case where a program read from a storage medium achieves the functions described in the first embodiment to the fourth embodiment, but also the case where an OS running on a computer executes some of or all functions described in the first embodiment to the fourth embodiment.

Furthermore, it will be appreciated that embodiments of the present invention include the case where, after a program read from a storage medium is stored in an add-on expansion board inserted in a computer or a memory of an add-on expansion board connected to a computer, the add-on expansion board or a CPU in the add-on expansion board executes some of or all functions described in the first embodiment to the fourth embodiment.

When the present invention is applied to the above-described program or the storage medium that stores the above-described program, the program includes, for example, program code that corresponds to a flow chart shown in the above-described FIG. 2, 3, 5, 9, 10, 11, or 13.

As many apparently widely different embodiments of the present invention can be made without departing from the spirit and scope thereof, it is to be understood that the invention is not limited to the specific embodiments thereof except as defined in the claims.

What is claimed is:

1. A radiation image processing apparatus for reconstructing a CT image from a plurality of image data items of a subject to be inspected, the image data items taken from different angles, comprising:
   body-movement information extracting means for extracting a structure constituting the subject from at least two image data items and obtaining at least one change indicating a body-movement of the subject based on the structure;
   repeat-radiograph determination means for determining whether or not a repeat radiograph is executed based on the at least one change; and
   CT reconstruction means for reconstructing a CT image from the plurality of image data items.

2. A radiation image processing apparatus according to claim 1, wherein the body-movement information extracting means extracts coordinates of the structure constituting the subject to be inspected from at least two of the image data items and calculates changes in the coordinates of the extracted structure.

3. A radiation image processing apparatus according to claim 2, wherein the coordinates of the structure constituting the subject to be inspected are coordinates of an outline of the structure and are normalized.

4. A radiation image processing apparatus according to claim 1, wherein the body-movement information extracting means extracts the structure constituting the subject to be inspected from at least two of the image data items and calculates an overlap area between two images of the structure as the change.

5. A radiation image processing apparatus according to claim 1, wherein the structure is one of a diaphragm, a lung area, and the subject to be inspected.

6. A radiation image processing apparatus according to claim 5, wherein the body-movement information extracting means calculates a change based on information extracted from an image data item of a first image and information extracted from an image data item of a second image taken from the reverse angle to the first image.

7. A radiation image processing apparatus according to claim 1, further comprising display means for presenting the change calculated by the body-movement information extracting means to an operator.

8. A radiation image processing apparatus according to claim 7, wherein, in the repeat-radiograph determination means, the operator determines whether or not a repeat radiograph is required based on the change presented by the display means.

9. A radiation image processing apparatus according to claim 1, further comprising an X-ray generation source for emitting radiation to the subject to be inspected, a rotating unit for relatively rotating the subject under the radiation emitted from the X-ray generation source, a two-dimensional X-ray sensor for converting the radiation to electrical signals, and a processing circuit for convening the electrical signals to an image data item, wherein a plurality of the image data items is output from the processing circuit.

10. A radiation image processing method for reconstructing a CT image from a plurality of image data items, the method comprising the steps of:
    extracting a structure constituting a subject to be inspected from at least two image data items and obtaining at least one change indicating a body-movement of the subject based on the structure;
    determining whether or not a repeat radiograph is executed based on the at least one change calculated in said extracting step; and
    reconstructing a CT image from the plurality of image data items.

11. A radiation image processing method according to claim 10, wherein the CT image is reconstructed when it is determined that a repeat radiograph is not executed.

12. A computer readable medium having a program for causing a computer to execute a predetermined method comprising:
    extracting a structure constituting a subject to be inspected from at least two image data items and obtaining at least one change indicating a body movement of the subject based on the structure;
    determining whether or not a repeat radiograph is executed based on the at least one change calculated in said extracting step; and
    reconstructing a CT image from the plurality of image data items.

13. A computer readable medium according to claim 12, wherein the CT image is reconstructed when it is determined that a repeat radiograph is not executed.

14. A radiation image processing apparatus for reconstructing a CT image from a plurality of image data items of a subject to be inspected, the image data items taken from different angles, comprising:
    a body-movement information extracting unit for extracting a structure constituting the subject from at least two image data items and obtaining at least one change indicating a body-movement of the subject based on the structure;
    a repeat-radiograph determination unit for determining whether or not a repeat radiograph is executed based on the at least one change; and
    a CT reconstruction unit for reconstructing a CT image from the plurality of image data items.

15. A radiation image processing apparatus according to claim 14, wherein the CT reconstruction unit starts reconstructing the CT image when it is determined that a repeat radiograph is not executed.

* * * * *